United States Patent [19]
Delmore et al.

[11] Patent Number: 5,620,095
[45] Date of Patent: Apr. 15, 1997

[54] ORTHOPEDIC CASTING MATERIAL AND HERMETIC PACKAGE

[75] Inventors: Michael D. Delmore, Moundsview, Minn.; Peter T. Dietz, Lake Forrest, Calif.; Rafael M. Yasis, White Bear Lake, Minn.

[73] Assignee: Minnesota Mining and Manufacturing Company, St. Paul, Minn.

[21] Appl. No.: 402,512

[22] Filed: Mar. 10, 1995

Related U.S. Application Data

[63] Continuation-in-part of Ser. No. 75,815, Jun. 11, 1993, abandoned, and Ser. No. 75,663, Jun. 11, 1993.

[51] Int. Cl.$^6$ ................................................. B65D 65/36
[52] U.S. Cl. ............................................ 206/438; 383/201
[58] Field of Search ...................... 206/363, 438, 206/484; 229/309–316; 383/200, 201, 205–208

[56] References Cited

U.S. PATENT DOCUMENTS

| | | | |
|---|---|---|---|
| 2,307,735 | 1/1943 | Fehr | 229/51 |
| 2,578,324 | 12/1951 | Southwick, Jr. | 183/4.8 |
| 2,956,723 | 10/1960 | Tritsch | 229/48 |
| 3,084,984 | 4/1963 | Adler | 312/31 |
| 3,127,087 | 3/1964 | Spees | 229/51 |

(List continued on next page.)

FOREIGN PATENT DOCUMENTS

| | | | |
|---|---|---|---|
| 0407056 | 1/1991 | European Pat. Off. | A61L 15/07 |
| 0471220 | 2/1992 | European Pat. Off. | B29C 47/06 |
| 0522824 | 1/1993 | European Pat. Off. | A61F 13/04 |
| 4000857 | 7/1991 | Germany . | |
| 4109605 | 9/1992 | Germany | B65D 75/62 |
| 4305662 | 9/1993 | Germany | B65D 30/02 |
| 56-123256 | 9/1981 | Japan | B65D 33/00 |
| 59-26450 | 2/1984 | Japan | B65D 33/00 |
| 60-13661 | 1/1985 | Japan | B65D 77/30 |
| 8600546 | 10/1987 | Netherlands | B65D 65/34 |
| 384452 | 11/1964 | Switzerland . | |
| 715997 | 9/1954 | United Kingdom | 94/1 |
| 2200286 | 8/1988 | United Kingdom | A61F 13/04 |
| WO86/02908 | 5/1986 | WIPO | B65D 75/58 |
| WO92/16431 | 10/1992 | WIPO | B65D 75/58 |

OTHER PUBLICATIONS

Noller; "Chemistry of Organic Compounds"; Ch. 6, pp. 121–122 (1957).

Primary Examiner—Jimmy G. Foster
Attorney, Agent, or Firm—Gary L. Griswold; Walter N. Kirn; Stephen W. Bauer

[57] ABSTRACT

A kit of curable orthopedic casting/splinting materials in a substantially hermetic heat sealed pouch formed from laminate sheet-material having a heat sealable inner layer bonded to an outer layer. The pouch includes a multiplicity of fibers that facilitate tearing the laminate sheet material in a predetermined direction. The multiplicity of fibers are disposed between the inner and outer layers of the laminate sheet material, and are generally equally spaced across the entire width of the material. A notch and a friction region are also preferably provided to facilitate tearing the pouch.

37 Claims, 4 Drawing Sheets

U.S. PATENT DOCUMENTS

| | | | |
|---|---|---|---|
| 3,272,424 | 9/1966 | Rodkey | 229/66 |
| 3,323,707 | 6/1967 | King | 229/66 |
| 3,485,349 | 12/1969 | Chaney, Jr. | 206/56 |
| 3,494,538 | 2/1970 | Matthews | 229/51 |
| 3,535,409 | 10/1970 | Rohde | 264/95 |
| 3,554,436 | 1/1971 | Palmer | 229/62 |
| 3,595,468 | 7/1971 | Repko | 229/66 |
| 3,608,566 | 9/1971 | Storandt | 132/84 |
| 3,630,194 | 12/1971 | Boardman | 128/90 |
| 3,648,704 | 3/1972 | Jackson | 128/349 |
| 3,759,439 | 9/1973 | Cross et al. | 229/66 |
| 3,770,122 | 11/1973 | Thiele | 206/84 |
| 3,873,735 | 3/1975 | Chalin et al. | 426/87 |
| 3,908,644 | 9/1975 | Neimart et al. | 128/90 |
| 3,932,526 | 1/1976 | Koshar | 260/607 |
| 4,131,114 | 12/1978 | Kirkpatrick et al. | 128/90 |
| 4,139,643 | 2/1979 | Hix et al. | 426/122 |
| 4,246,288 | 1/1981 | Sanborn, Jr. | 426/122 |
| 4,279,344 | 7/1981 | Holloway, Jr. | 206/631 |
| 4,411,262 | 10/1983 | von Bonin et al. | 128/90 |
| 4,433,680 | 2/1984 | Yoon | 128/90 |
| 4,441,262 | 4/1984 | Gazzoni | 34/57 |
| 4,502,479 | 3/1985 | Garwood et al. | 128/90 |
| 4,598,826 | 7/1986 | Shinbach | 206/620 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,696,404 | 9/1987 | Corella | 206/604 |
| 4,718,556 | 1/1988 | Hildebrandt | 206/604 |
| 4,720,366 | 1/1988 | Binnersley et al. | 264/172 |
| 4,769,202 | 9/1988 | Eroskey et al. | 264/166 |
| 4,774,937 | 10/1988 | Scholz et al. | 128/90 |
| 4,781,297 | 11/1988 | Abrahamsson et al. | 206/610 |
| 4,801,042 | 1/1989 | Hamada et al. | 220/410 |
| 4,834,245 | 5/1989 | Ohga et al. | 206/610 |
| 4,841,958 | 6/1989 | Ersfeld et al. | 128/90 |
| 4,883,625 | 11/1989 | Glemet et al. | 264/136 |
| 4,903,841 | 2/1990 | Ohsima et al. | 206/604 |
| 4,903,843 | 2/1990 | Fischer | 206/609 |
| 4,927,010 | 5/1990 | Kannankeril | 206/204 |
| 4,940,047 | 7/1990 | Richter et al. | 128/90 |
| 4,984,566 | 1/1991 | Sekimo et al. | 128/90 |
| 5,014,403 | 5/1991 | Buese | 28/170 |
| 5,027,803 | 7/1991 | Scholz et al. | 128/89 |
| 5,063,639 | 11/1991 | Boeckmann et al. | 24/30.5 |
| 5,139,593 | 8/1992 | Loubineux et al. | 156/73.2 |
| 5,310,587 | 5/1994 | Akahori et al. | 428/35.2 |
| 5,346,939 | 9/1994 | Moren et al. | 524/176 |
| 5,353,486 | 10/1994 | Schmidt et al. | 28/167 |
| 5,454,601 | 10/1995 | Sekine et al. | 383/200 |

ORTHOPEDIC CASTING MATERIAL AND HERMETIC PACKAGE

This application is a continuation-in-part of application Ser. No. 08/075,815, filed Jun. 11, 1993, now abandoned, and of application Ser. No. 08/075,663, filed Jun. 11, 1993, pending.

BACKGROUND OF THE INVENTION

The present invention relates to the field of orthopedic splinting/casting materials and packaging for the same. More particularly, the present invention relates to curable orthopedic splinting/casting material in a heat sealed hermetic package which includes means for facilitating tearing of the package in a predetermined direction.

Hermetic packaging constructed from heat sealable laminated materials is well-known. Many products are placed in such packages to extend their shelf life by sealing the products from exposure to air, water vapor, etc. Heat sealed hermetic packaging constructed from laminated sheet materials is especially popular because of its relatively low cost as compared to effectiveness.

The hermeticity of such packages is especially important in the field of packaging for curable orthopedic splinting/casting materials. Such products are discussed in U.S. Pat. Nos. 4,433,680; 4,609,578; 4,667,661; 4,774,937; and 5,027,803, all of which are hereby incorporated for their disclosures relating to those materials. Briefly, however, such products are extremely sensitive to ambient levels of water vapor and will harden (i.e., "cure") upon exposure to very low levels of water vapor. Once hardened, the product can no longer be used for its intended purpose and must be discarded. Because of their sensitivity, such products are typically packaged in single-use hermetic packages as constructed from composite laminate sheet materials.

Hermetically sealed packages constructed from laminated sheet materials are, however, typically difficult to open due to the nature of the materials used to manufacture them. The laminated sheet materials typically comprise three or more layers chosen for their strength, moisture impermeability, and/or heat sealability. The composite material is difficult to tear and is particularly difficulty to tear in a desired direction. As a result, users must typically first tear the package once and additionally tear, cut or, for example, open one of the heat sealed ends to provide a large enough opening to allow adequate access to the product inside.

One attempt to provide heat sealed hermetic packages which provide predictable tearing characteristics is discussed in U.S. Pat. No. 4,598,826. Tear strips are laminated to the interior of the package to facilitate tearing of the package in a desired direction lying along the tear strips. Such packages are, however, difficult to manufacture as the tear strips must typically be introduced as the package is formed from the laminated sheet material. In addition, the hermeticity of the packages can be compromised if the tear strips are included in the heat seals because of their relatively large profile which is difficult to accommodate in the heat seals without forming leaks.

Another attempt at addressing the difficulties in opening such packages includes forming heat sealed packages with lines of weakness across one of the heat seals as described in U.S. Pat. No. 4,139,643. The lines of weakness are provided to enhance the predictability of opening the packages. One disadvantage of this approach is that the package can only be predictably opened along the heat seals. In many instances that opening is not large enough to provide sufficient access to the product without further tearing or cutting to enlarge the opening in the package.

Another disadvantage of providing lines of weakness is the opportunity that they present for leaks into the package. Such features may be particularly vulnerable to flex cracking which can break the thin foil vapor barrier layer used in the laminate sheet materials.

Yet another approach to providing predictable opening characteristics for heat sealed hermetic packages is described in U.S. Pat. No. 4,279,344. The packages discussed in that reference include a heat sealable inner layer, metal foil vapor barrier layer and outer layer to protect the metal foil. The heat sealable inner layers form a peelable bond which is easily separated by the user. One disadvantage to this approach is that the bond formed is designed to be weak enough to allow for easy separation which can lead to failure of the package to maintain its hermeticity during shipping and handling.

European Patent Publication No. EP 0 471 220 discloses an "easily tearable film and pouch made therefrom". The film has an easily tearable thin walled part incorporating two strings into the plastic film, both of which are generally adjacent one edge of the pouch. Notches are provided between the two strings.

See, also, U.S. Pat. Nos. 2,307,735; 3,323,707; 3,494,538; 3,759,439; 4,720,366; 4,834,245; 4,883,625; 4,769,202; 4,903,841; 4,903,843; and 5,139,593; Japanese Patent Publication Nos. 123256/1981; 26450/1984 and 13661/1985; German Patent Publication No. DE 41 09 605; Netherlands Patent Publication No. NL 8600546; Swiss Patentschrift No. 384,452; and PCT International Patent Publication No. 92/16431.

SUMMARY OF THE INVENTION

The present invention provides curable orthopedic casting/splinting materials in a substantially hermetic heat sealed package formed from laminate sheet material having a heat sealable inner layer bonded to an outer layer. The package includes means for facilitating tearing of the laminate sheet material in a predetermined direction. The means for facilitating tearing comprises a multiplicity of generally parallel fibers disposed between the inner and outer layers of the laminate sheet material and lying substantially along the predetermined direction. The fibers extend in the longitudinal direction of the web from which the package is formed, and are substantially equally spaced apart across the entire width of the web. As used herein, "multiplicity" means at least three fibers.

Each fiber of the tearing means provides a path along which the laminate sheet material of the package predictably tears when opened. The path extends along a direction which is sufficiently long to provide easy access to the product in the package.

The ability to provide predictable opening properties is especially useful in packaging for orthopedic splinting/casting materials because such packages are typically opened at the point of use to limit the product's exposure to moisture. In addition, easy access to the product in the package further limits the time needed to remove the product and, therefore, the product's exposure to moisture.

Furthermore, the ability to provide such properties without compromising the hermeticity of the package is particularly advantageous.

The preferred laminate sheet material comprises an inner heat sealable layer laminated to a metal foil layer which provides the desirable moisture-proof properties of the laminate. The outer surface of the metal layer is bonded to an outer layer which preferably provides toughness and puncture resistance to protect the vapor barrier properties of the metal foil.

In one aspect of the invention, the fibers are laminated between the metal foil and outer layer. In that embodiment, the impact of the fibers on the heat seals is minimized because the fibers are farther from the heat sealed inner layers.

In another aspect of the invention, the fibers are laminated between the metal foil and the inner layer. In that embodiment, the fibers are better able to tear the metal foil layer, leading to more predictable tearing characteristics.

Most preferably, the means for facilitating tearing further comprise at least one friction region positioned on the outer surface of the outer barrier film and a cut located near the edge of the package and near the friction region suitable for facilitating tearing the package even when the outer surface of the package is contacted with a lubricant. The friction region provides a sufficient static friction when the outer surface of the package has been contacted with a lubricant to facilitate easily tearing open the package.

The friction region preferably comprises an adhesively backed paper material providing a mean immediate total static friction of at least 100 grams when contacted with lubricant.

The friction regions of the present invention are positioned to provide a sufficient grip for each hand (i.e., a separate grip region for each hand on each side of the cut) thereby allowing for the easy tearing of the sheet when a lubricant has contacted the package. More preferably, the friction regions, in addition to being on both sides of the cut, are positioned on both sides of the package (i.e., a first friction region on the thumb side of the package and a second friction region on the finger side of the package).

Most preferably, the cut is provided in the heat seal at one end of the package between adjacent fibers, and a friction region on both sides of the package adjacent the cut.

In one preferred embodiment of the invention the friction regions are provided as a pair of matte-finish (i.e., non-glossy) paper "labels" adhered to the outer surface of the package. The labels are adhered to the package crossing a cut (e.g., using a pressure sensitive adhesive or a hot-melt rubber cement) and on opposite sides of the package. If desired a single suitable label may be wrapped or folded over the edge of the package and thereby adhere to both outer surfaces of the package (i.e., "on opposite sides" as previously mentioned).

Other features will be pointed out hereinafter.

DETAILED DESCRIPTION OF THE PREFERRED AND ALTERNATE EMBODIMENTS

Figure 1:
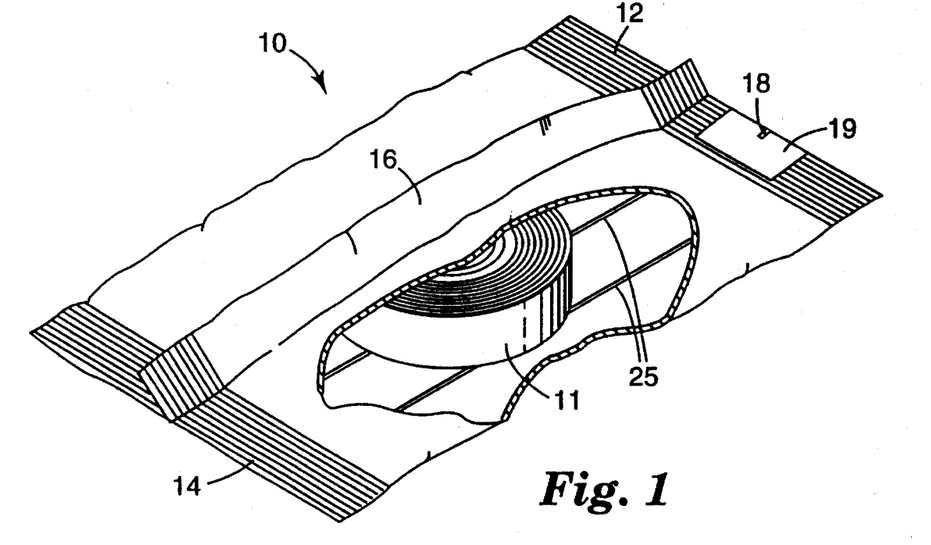
FIG. 1 is a perspective view, partially cut-away, of one embodiment of a package containing curable casting/splinting material according to the present invention.

FIG. 1 depicts one embodiment of a pouch constructed of a laminate sheet material and containing a roll of curable casting/splinting material according to the present invention. As shown there, the pouch 10 includes end seals 12 and 14 and a fin seal 16 running lengthwise along the pouch 10. The pouch 10 also preferably includes a notch 18 to facilitate opening of the pouch 10, and most preferably includes a friction region 19 on both sides of the notch 18 as discussed below with respect to FIGS. 6–10. The pouch 10 is formed of laminate sheet material 20 which is discussed more fully below.

Located within the pouch is a roll of curable casting/splinting material 11. The preferred material 11 is moisture-curable and, most preferably, includes an isocyanate-functional resin which cures when exposed to moisture. Furthermore, although a roll is depicted in FIG. 1, it will be understood that the material 11 could be provided as a plurality of rolls or one or more flat sheets of material. Suitable curable casting/splinting materials are described in, for example, U.S. Pat. Nos. 4,433,680; 4,609,578; 4,667,661; 4,774,937 and 5,027,803; all of which are incorporated by reference above. Those disclosures should not, however, be construed as limiting the scope of curable materials for packaging according to the present invention.

Although in the preferred embodiment, pouch 10 comprises two end seals 12 and 14 and a fin seal 16 (commonly referred to as a form, fill and seal pouch), it will be understood that hermetic heat sealed packages designed to incorporate laminate sheet material according to the present invention could take many forms and that the form described with respect to the preferred embodiment is only one version of the same. Alternate types of packages could include, but are not limited to, flat, two-dimensional pouches or three-dimensional, stand-up gussetted pouches.

Figure 2:
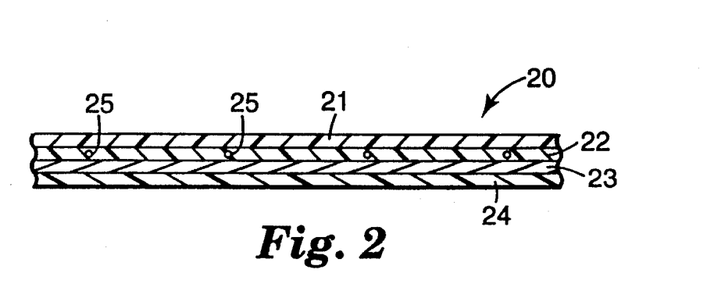
FIG. 2 is an enlarged partial cross-sectional view of one embodiment of a laminate for use in packages constructed according to the present invention.

FIG. 2 depicts an enlarged cross-sectional view of a portion of one embodiment of laminate sheet material used in a preferred embodiment of a package according to the present invention. The laminate 20 is a composite structure comprising layers 21, 22, 23 and 24. In the embodiment shown, layer 23 provides a vapor barrier through which air and water vapor transmission is severely limited.

Layers 21 and 22 preferably comprise a protective layer over the vapor barrier layer 23. Examples of potential materials for layers 21 and/or 22 include puncture resistant paper or plastic resin material. It is preferred that one of the outer protective layers is comprised of at least one layer of polyester, nylon or polypropylene which protects the preferred aluminum foil vapor barrier layer 23 from punctures and tears during shipping and handling.

In one preferred embodiment, outer layer 21 comprises biaxially oriented polypropylene (BOPP) having a thickness of 0.001 inch (0.025 millimeter). A layer 22 of ethylene acetate acrylic (EAA) having a thickness of 0.001 inch (0.025 millimeter) is bonded to one side of the layer 21 of BOPP to enhance the bonding of the BOPP outer layer 21 to the vapor barrier layer 23.

The EAA layer 22 is bonded to the vapor barrier layer 23 of aluminum foil (in the preferred embodiment) with a thickness of 0.00035 inch (0.00889 millimeter).

Although the preferred vapor barrier layer 23 is aluminum foil which is entirely free of even minute holes, it is known that such foils remain highly impervious to air and water vapor transmission even when they include a few widely scattered minute openings. In other words, by highly impervious it is meant that as little air and water vapor as possible can pass through the minute openings found in currently available metal foils used in laminate sheet material for packaging.

Furthermore, it will be understood that other materials can be substituted for the preferred aluminum foil provided they supply the necessary vapor barrier without significantly affecting the flexibility or heat/sealability of the laminate 20. Examples of alternate materials include, but are not limited to, metallized films, poly-vinylidene chloride coated films (e.g., SARAN™ coating), and ACLAR™ high moisture vapor permeable films (available from Allied Signal Inc., Morristown, N.J.).

Bonded to the inside surface of vapor barrier layer 23 is an inner layer 24 of heat sealable material comprising a plastic resin film such as polypropylene, polyethylene or a polyethylene-polypropylene copolymer that is extruded and/or calendared directly onto layer 23. Most preferably, the heat sealable inner layer 24 is SURLYN™ brand resin (#1702) available from E. I. DuPont deNemours & Company, Wilmington, Del. It will, however, be understood that many other heat sealable materials could be substituted for the preferred variety. Examples of alternate materials include, but are not limited to, other polyethylenes, EAA or any low melting point thermoplastic material.

Inner layer 24 also preferably provides a barrier to prevent chemical reactions between the product in the packages and the vapor barrier layer 23. It also provides puncture and abrasion resistance to protect layer 23 from the product contained in any package formed from the laminate sheet material 20.

In the embodiment illustrated in FIG. 2, a multiplicity of fibers 25 are contained within layer 22. The fibers 25 are preferably equally spaced apart on one inch (25 mm) centers across the width of the packaging material. The preferred fiber 25 is a multi-fiber glass filament, although a monofilament fiber could be substituted. Multiple fiber filaments are generally preferred because their tensile strength is typically greater (for a given outside diameter) than the tensile strength of a monofilament fiber. The preferred fiber has a nominal diameter of 0.00033 inch (0.00838 millimeter/99 denier). It is constructed of glass fibers and has a tensile strength of 1.7 lbs. (0.77 kilogram). The preferred fibers are available from Owens Corning Fiberglas Company, Toledo, Ohio, under the designation ECD 450 1/0, although other similar fibers, including monofilament fibers, may be substituted provided their tensile strength to outside diameter ratio is sufficient for tearing as described below. In addition to multi- or mono-filament fibers, it will also be understood that the fibers can be of many different materials other than glass. Examples of alternate fiber materials include, but are not limited to, nylon, polyester, graphite and, aramid, such as available under the trademarks "KEVLAR™" or "NOMEX™" from E. I. DuPont deNemours & Company, Wilmington, Del.

The provision of fibers 25 each of which has a relatively small diameter when compared to its tensile strength is important to operation of the present invention. The fibers 25, when inlaid into a laminate across a web preferably produce a laminate having a very flat cross-web profile. As a result, the roll is free of any visible signs of gauge band when the finished laminate is wound onto a roll. Gauge band is a phenomena which occurs with extruded laminates when the extrusion materials are not evenly distributed across the web. Uneven distribution of the cross web material can cause difficulties when the laminate is wound into finished roles which can telescope or otherwise be unstable.

Furthermore, the size of the fibers 25 is preferably also small to minimize the effect of the fibers 5 in the heat seals 12 and 14 located at the ends of the preferred embodiment of the pouch 10 depicted in FIG. 1. Fibers 25 having large diameters could provide the opportunity for leakage at any heat seals in packages constructed with laminate sheet material according to the present invention.

When opened, the pouch 10 preferably tears along one or more of the fibers 25 located within the laminate sheet material 20 forming the pouch 10. It is contemplated that one or more of the fibers 25 may break during the tearing process. In that situation, the tear line will typically migrate to an adjacent fiber 25 and continue tearing along the length of the package 10. Whether the tear in the package follows the initial fiber 25 or whether the tear migrates to another fiber 25, the pouch 10 will typically be opened substantially along its full length, thereby allowing easy access to any product contained therein.

Figure 3:
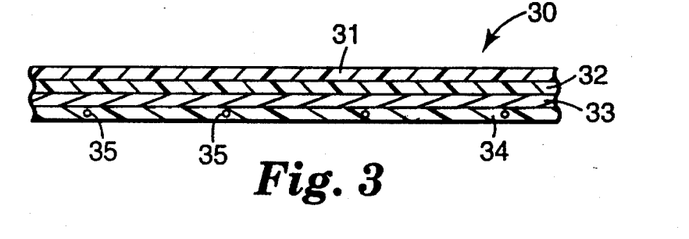
FIG. 3 is a an alternate embodiment of a laminate for use in packages constructed according to the present invention.

An alternate embodiment of a laminate sheet material 30 according to the present invention is depicted in FIG. 3. The laminate sheet material 30 comprises outer layers 31 and 32 bonded to a vapor barrier layer 33. As with laminate sheet material 20 in FIG. 2, outer layers 31 and 32 preferably combine to form a protective, puncture-resistant layer over the vapor barrier layer 33 to prevent punctures and tears of that layer 33 during handling.

On the opposite side of layer 33 is a heat sealable layer, preferably of SURLYN brand resin available from E. I. DuPont deNemours & Company, Wilmington, Del., which is used to heat seal packages formed using laminate sheet material 30.

In this embodiment, the heat seal layer 34 preferably incorporates fibers 35 as opposed to locating the fibers in the outer layers as described with respect to laminate sheet material 20 in FIG. 2 above. In all other aspects, the laminate sheet material 30 of FIG. 3 is similar to the laminate sheet material 20 of FIG. 2.

In each of the embodiments of laminate sheet materials 20 & 30 described above, the preferred materials used to manufacture the products consisted of the following: the biaxially oriented polypropylene film (BOPP) is available from Mobil Chemical Corp., Films Division, Pittsford, N.Y., under the designation 100 Dicot LBW. In both embodiments it is provided with a thickness of 0.001 inches (0.025 mm). The surfaces of the BOPP material are provided with treatments to increase its adhesion to materials such as ethylene acetate acrylic (EAA).

The EAA material is available from Dow Chemical, Midland, Mich., under the designation Primacor 3440 and is tinted with 5% (by weight) white $TiO_2$ available from Spectrum Color, Minneapolis, Minn. The EAA is coated to a thickness of 0.001 inches (0.025 mm).

The aluminum foil is available from Allfoils, Inc., Cleveland, Ohio under the designation type 1145, "A" wettability, with a thickness of 0.35 mil (0.00889 millimeter).

The inner heat sealable layer is preferably SURLYN brand resin, available from DuPont as described above. It is preferably modified with an anti-block compound, also available from E. I. DuPont, under the designation Conpol 5B10S1.

It will, of course, be understood that many other materials could be used to form the laminate sheet materials used in packages according to the present invention and that the preferred materials described above should not be construed as limiting the scope of the invention.

The laminate sheet materials used in packages constructed according to the present invention are manufactured in processes similar to those used to manufacture known laminate sheet materials incorporating metal foil vapor barriers where no fibers are present. Such manufacturing techniques are well known to those skilled in the art of producing packaging laminates and will not be described in detail herein.

Figure 4:
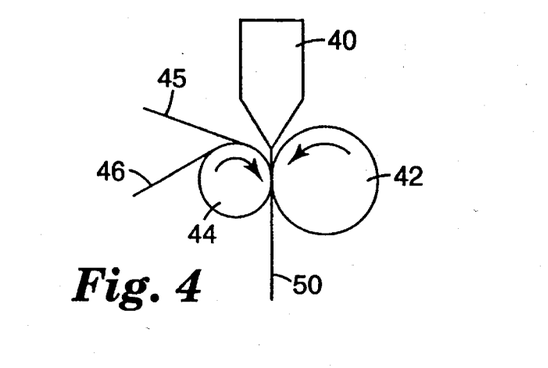
FIG. 4 is a schematic diagram of one process of manufacturing one embodiment of a laminate for use in packages according to the present invention.

FIG. 4 does, however, illustrate a schematic diagram of one method of manufacturing a laminate sheet material 50 according to the present invention. As shown there, the method of manufacturing the embodiment of laminate sheet material 30 (see FIG. 3) is depicted.

To begin, a sheet of biaxially oriented polypropylene (BOPP) is extrusion mounted using a layer of EAA to the preferred barrier material, i.e., aluminum foil in the preferred embodiment. That composite laminate 46 (consisting of BOPP/EAA/foil) is then directed over nip roll 44 which runs between a chilled textured roll 42, both of which rotate as depicted. The foil side is exposed as laminate 46 runs over roll 44. An extrusion coater 40 deposits a layer of the preferred heat seal material (SURLYN resin #1702) into the nip formed between rolls 42 and 44. Also directed over nip roll 44 are the fibers 45 according to the present invention.

The process depicted in FIG. 4 results in the ends of fibers 45 being contained within the heat seal layer of the laminate sheet material 50 produced by this method.

Alternately, it will be understood that fibers 25 depicted in FIG. 2 could be similarly mounted in a layer of EAA which is extrusion coated onto the vapor barrier 23 depicted in FIG. 2. In one preferred process, the layer 21 of biaxially oriented polypropylene (in the preferred embodiment) is extrusion coated over the layer of EAA 22 and fibers 25. The heat seal layer 24 of SURLYN resin or a similar material can be extrusion coated onto the vapor barrier layer either before or after the EAA and BOPP layers have been bonded to the opposing side of the vapor barrier layer 23.

Figure 5:
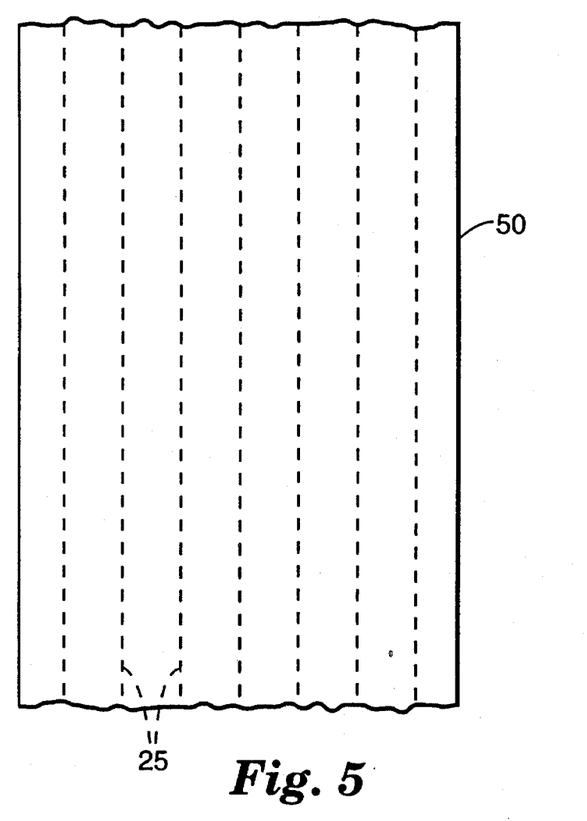
FIG. 5 is a top plan view of a sheet of a laminate material that is used to form the packages constructed according to the invention.

FIG. 5 illustrates a sheet 50 of laminate material having a multiplicity of generally parallel fibers 25. The multiplicity of fibers 25 are substantially equally spaced apart across substantially the entire extent of the laminate material of the pouch in the second direction (e.g., width). The first direction (e.g., length) is the direction extending between the end seals of the pouch. The multiplicity of fibers 25 comprises a sufficient number of fibers 25 such that the fibers 25, which extend generally in the longitudinal direction of a continuous web 50 of the laminate material, can be provided in substantially equal spaced-apart relationship across the entire width of the web 50. One advantage of the arrangement of spaced-apart, parallel fibers 25 is that it facilitates rolling up the laminate material 50 into rolls before cutting and heat sealing the material into packages. The substantially equally-spaced apart arrangement eliminates gauge band and telescoping of the rolled material, thereby increasing stability of the roll. It is believed that, if such fibers were offset toward one end edge or the other of the web, a rolled up web would be tight adjacent one edge and loose adjacent the other, resulting in an unstable roll that would not work with subsequent processing machines. Such unstable rolls would result in the web material jamming in subsequent processing. Another advantage of this construction is that, if one fiber 25 breaks, the tear will be guided by an adjacent fiber 25 across substantially the entire length of the pouch.

FIGS. 6–11 illustrate aspects of a preferred technique for facilitating gripping the package to tear the package. See, for example, co-pending, co-assigned U.S. patent application Ser. No. 08/075,663, filed Jun. 11, 1993, by Peter T. Dietz, on "Orthopedic Casting Article with Easy Open Package", which is hereby incorporated herein by reference.

As discussed in U.S. patent application Ser. No. 08/075,663, kits of orthopedic casting material include a lubricant for reducing the tack of the curable casting material (e.g., reducing the tack between the activated curable casting material and a gloved hand). The lubricant may be present in the kit as described in any one of the following embodiments. For example, the lubricant may be provided as part of the curable resin system, as a separate component which is added to the activator (e.g., added to a water dip), or as a coating to a glove which is designed to transfer lubricant to the activator or casting material during the activation of the resin and/or the wrapping of the cast. Alternatively, the lubricant may be provided as a coating to a glove that otherwise reduces the tack of the casting material by providing a slippery glove surface. As used herein a "kit" refers to a combination of articles or ingredients which are sold as a unit or a combination of articles or ingredients which are designed to be used together in a method of immobilizing a limb. For example, a "kit" includes the combination of a glove or a package of gloves comprising a lubricant and a package of the present invention containing a casting material.

The lubricant may be provided as part of the resin in accordance with U.S. Pat. No. 4,667,661, which is herein incorporated by reference, such that the casting materials exhibit reduced tack prior to and during cure and yet form a cast with acceptable strength and lamination strength. Suitable lubricants include: hydrophilic groups which are covalently bound to the resin system; additives which are incompatible with the curable resin including: a surfactant, a polymer comprised of a plurality of hydrophilic groups, and a polysiloxane; and combinations of the above.

When the lubricant is initially provided "inside" the package (e.g., associated with the casting material or otherwise sealed within the pouch) the outer surface of the first opened package is likely not to be contacted with lubricant prior to being opened. However, the utility of the present invention will readily be apparent when one attempts to open a second package. In this case the lubricant from the casting material of the first opened package is then available to contact the applier's gloves or mix with the activator solution, etc. The lubricant from the first opened package will then be available for contact with the outer surface of the second unopened package and thereby render the outer surface of the second package slippery. Alternatively, when the lubricant is initially provided "outside" the package (e.g., as a coating for a glove or as an additive to the activator solution) it is available for contact with the first opened package and can thereby render the outer surface of the first, and any subsequent, package slippery.

Figure 6:
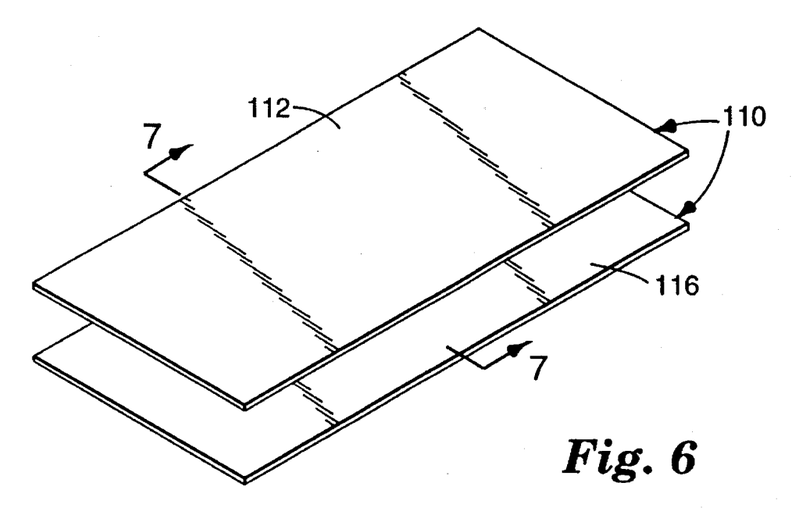
FIG. 6 is a fragmented, perspective view of a suitable laminate sheet material of the present invention.
Figure 7A:
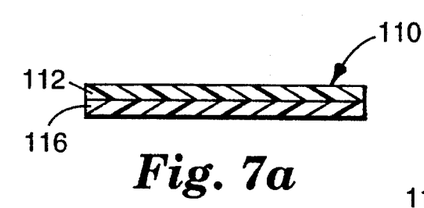
FIGS. 7a, 7b, and 7c are greatly enlarged cross-sectional views of the laminate sheet material of FIG. 6 taken approximately along the line 7—7 of figure 6.
Figure 7B:
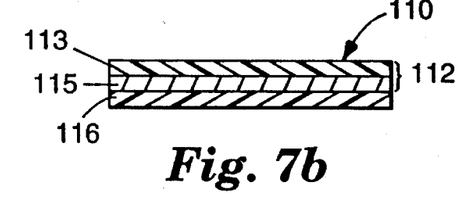
Figure 7C:
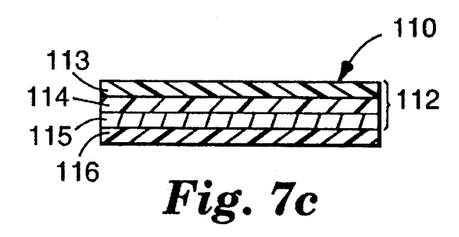

Referring now to FIGS. 6 and 7(a–c) of the drawings, there is shown, in perspective view in FIG. 6 and in cross-sectional view in FIGS. 7a, 7b, and 7c, a laminate sheet material 110 used to form the package. As seen in FIG. 7a, the laminate sheet material 110 is comprised of an outer barrier film 112, and a heat-sealable inner film 116. As seen in FIG. 7b, the outer barrier film 112 is comprised of a puncture resistant outer material 113, and an intermediate layer 115. As seen in FIG. 7c, the laminate sheet material 110 further comprises a bonding layer 114 which serves to bond the outer material 113 and the intermediate layer 115.

As used here, the outer material 113 of the outer barrier film 112 is analogous to the outer layer of FIGS. 2 and 3, and the intermediate layer 115 of the outer barrier film 112 is analogous to the interior layer of FIGS. 2 and 3.

The sheet material 110 is comprised of conventional materials that are pressure and/or adhesive laminated together as will next be described. Intermediate layer 115 of sheet material 110 is preferably comprised of a metal foil that is highly impervious to air and water vapor. Preferably, the intermediate layer 115 is comprised of an aluminum foil having a thickness between 0.002 and 0.03 mm, more preferably between 0.005 and 0.015 mm, and most preferably between 0.007 and 0.010 mm. Although it is preferred that such aluminum foil be entirely free of even minute holes, it is known that such aluminum foil remains highly impervious to air and water vapor transmission even when having a few widely scattered, minute openings there through. By highly impervious, then, it is meant that as little as possible air and water vapor can pass through minute openings occurring in currently available metal foils. The outer barrier film 112 of the laminate sheet material 110 comprises a protective, puncture-resistant paper or plastic resin material. Preferably, the outer barrier film 112 is comprised of a polyester or a polypropylene film that is laminated to the aluminum foil of the intermediate layer 115 by conventional extrusion or adhesive bonding. For example, a bonding layer 114 may be utilized to bond the outer material 113 to the intermediate layer 115. Suitable bonding layer materials comprise low density polyethylene materials (hereinafter referred to as "LDPE") preferably having a density between 0.91 and 0.93 g/cc. The heat-sealable inner film 116 of the sheet material 110 is comprised of a heat-sealable material which can be laminated onto the aluminum foil of the intermediate layer 115 by adhesives, extrusion or the like. Preferably, the heat-sealable material is a plastic resin film such as a polypropylene, a polyethylene or a polyethylene-polypropylene copolymer that is extruded and/or calendared directly onto the aluminum foil. Most preferably, the heat-sealable material is "Surlyn"™ brand ionomer resin available from DuPont deNemours & Co. (Inc.), Wilmington, Del. which is extruded and/or calendared directly onto the aluminum foil. Fibers of the type discussed above may be incorporated into the bonding layer 114 or other layer.

Figures 8A, 8B, 9:
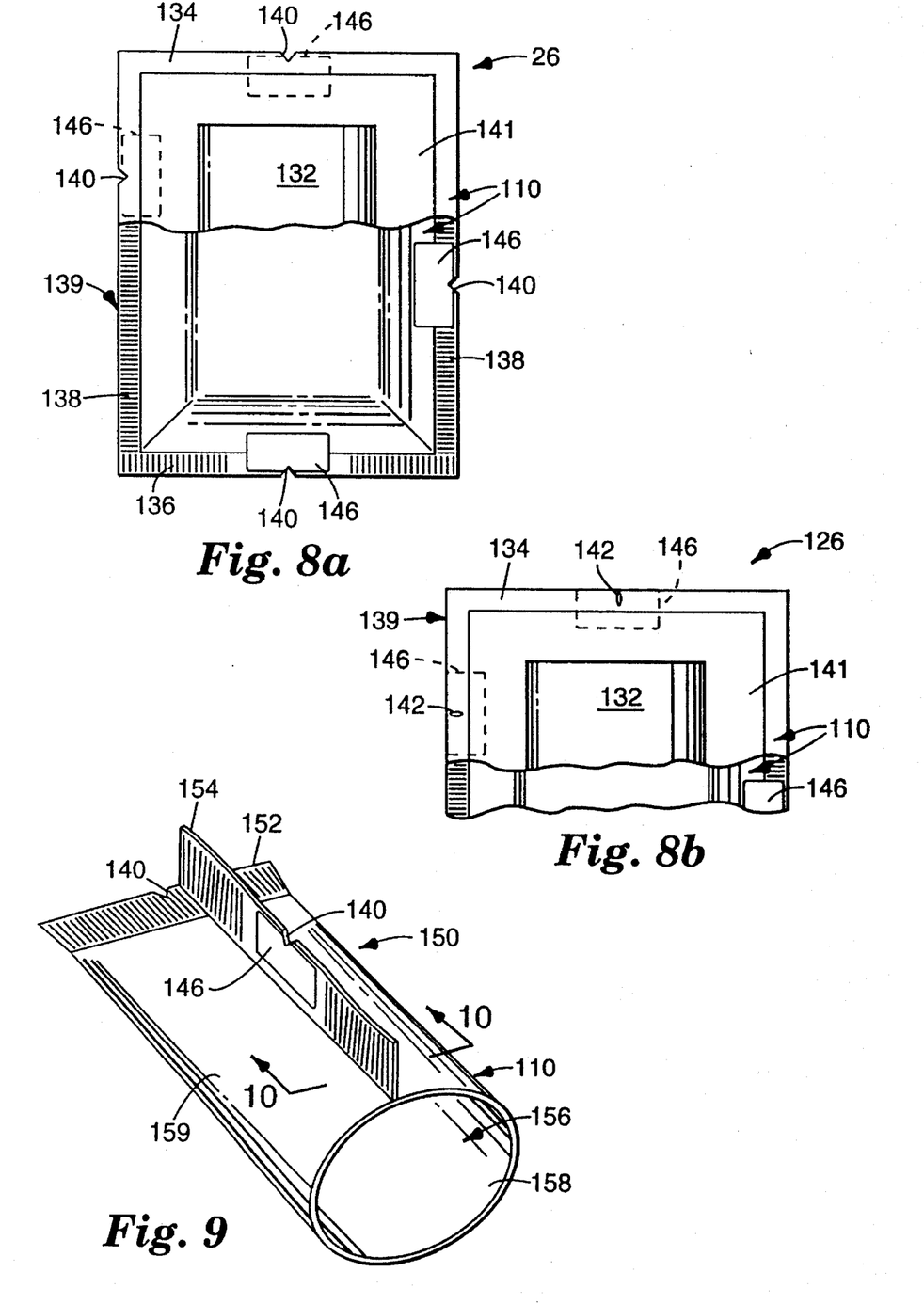
FIG. 8a is a plan view of one embodiment of the package of the present invention with portions broken away to show an object therein.
FIG. 8b is an enlarged, fragmented plan view depicting a cut wholly contained within the seal region.
FIG. 9 is a perspective view of an alternative embodiment of the package of the present invention.

FIG. 8a shows in plan view a first embodiment of a package 126 of the present invention formed from the laminate sheet material 110. The package 126 can be generally formed from a single piece of sheet material 110 or two pieces of sheet material 110. The package 126 is generally formed by peripherally heat sealing the sheet material 110 to itself or to a second piece of sheet material 110.

Still referring to FIG. 8a, there is shown the package 126 partially broken away to expose a sheet of curable casting material 132 otherwise hermetically sealed therein. As already described, the package 126 includes one or two pieces of sheet material 110 peripherally heat sealed together at two end heat seals 134 and 136 and two side heat seals 138 to form a pouch 139 having interior walls 141. The seals 134, 136, and 138 provide stiffened portions of the pouch 139 that are highly impervious to air and water vapor. By highly impervious, it is meant that as little as possible, and preferably no air and water vapor passes through these stiffened portions of the pouch 139.

Within one or more of the end heat seals 134 and 136 or the side heat seals 138 are one or more cuts 140 for facilitating the tearing of the package 126. Presently preferred cuts comprise a notch at the edge of the pouch in the seal region. The shape of the notch can be any shape (such as, for example, a "V" shaped notch or a thin slit) which effectively concentrates an applied stress and thereby facilitates the tearing or fracture of the laminate sheet material. Preferably, the cut is near the edge of the pouch. Alternatively, and as depicted in FIG. 8b, the cut 142 may be contained within a heat seal and not at the free edge of the package. In this embodiment (i.e., where the cut is near but not at the edge of the package) the cut serves to concentrate an applied stress at two points and thereby initiate two tears. The first tear propagates towards the edge of the package while the second tear propagates away from the edge of the package and thereby open the pouch portion.

Figure 10:
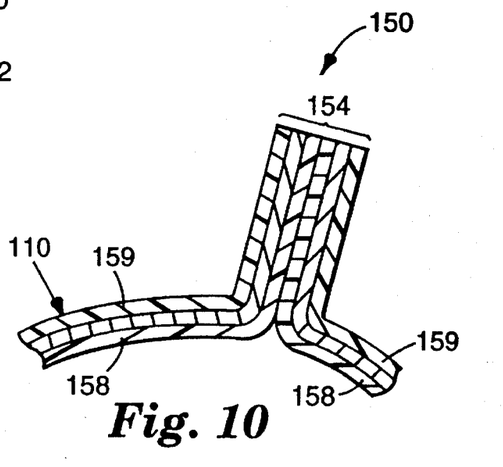
FIG. 10 is an enlarged, fragmented, cross-sectional view of the embodiment of FIG. 9 taken approximately along the line 10—10 of FIG. 9.

FIGS. 9 and 10 of the drawings show an alternative embodiment of the package of the present invention. Referring first to FIG. 9, a package 150 is shown in perspective view to be generally of a conventional fin-seal construction. The package 150 is conventionally formed around the sheet of curable casting material 132, shown in FIG. 8, from a single sheet of laminate sheet material 110 to have a fin seal 154 and a first end heat seal 152 to form a pouch 156 containing the sheet of curable casting material 132. The fin seal 154 provides a stiffened portion of the pouch 156.

The pouch 156 has an interior wall 158 and an exterior wall 159. Within the heat seal 152 is a cut 140 (or alternatively 142) for facilitating tearing the package 150 of the embodiment. The package 150 is completed by heat sealing the pouch 156 at the end opposite the heat seal 152. In so doing, a second cut similar to the cut 140 can be provided. Alternatively, the cut may be provided along the aforementioned fin seal 154.

Near the aforementioned cut 140 or 142 are friction regions 146 adapted to the outer surface of the pouch. The friction region 146 may be either a continuous region having a substantially uniform static coefficient of friction ("SCOF") over the region or a non-continuous region having areas of varying coefficients of friction. In general, the friction region 146 should be large enough to provide a sufficient "grip" (i.e., total static friction) when a lubricated sheet is pressed between a thumb and finger to allow the sheet material to be torn. In particular, the grip provided by the friction region 146 should be sufficient to facilitate the tearing of the package when the outer surface of the package has been contacted with the aforementioned lubricant.

The size of the friction region 146 should be large enough to provide the necessary static friction to achieve the tearing of the package. In general, the friction region is preferably as large as the contact area of the average human thumb and/or finger print. Preferably, the friction region 146 has a minimum area on each side of the cut of at least 10 mm×10 mm, and more preferably at least 20 mm×20 mm. If desired, the friction region 146 can be larger than this size and may encompass the total surface area of the package. Furthermore, it is not intended that the geometry of the friction region 146 be restricted to rectangular shapes. If desired circular, oval, triangular, or other geometries of similar surface area may be employed.

The friction region 146 refers to that region on the outer surface of the package which has a suitably high coefficient of friction to facilitate tearing of the package even when the friction region 146 has been exposed or contacted with a lubricant as described herein. The friction region 146 may comprise a separate layer or layers of a high coefficient of friction material bonded to the outer material 113 or may comprise an outer material having a suitably toughened outer surface. Presently preferred are friction regions which comprise a separate layer of a suitable material (e.g., a material having a suitably high coefficient of friction) bonded to the outer material of the package.

Suitable friction region materials include label materials (e.g., adhesively backed paper materials), and texturized materials (e.g., texturized plastic materials, sandpaper, etc.). The friction region materials may be adhesively bonded or mechanically affixed to the laminate packaging material or incorporated directly into the laminate. Suitable label materials include matte-finished and gloss-finished paper materials. Although not intending to be bound by theory, gloss-finished paper materials are presently less preferred as the gloss-finish is believed to delay absorption of the lubricant solution and thus cause the gloss-finished material to initially present a relatively low static friction when contacted with a lubricant solution. In contrast, matte-finish paper materials provide high static friction immediately upon contact with the lubricant and are preferred for use in the present invention. If desired, gloss-finished paper materials may be utilized provided the user wait a period of time to let the necessary static friction develop. Preferred matte-finish label materials for use as the friction region include "Premium matte coated litho—permanent adhesive" C1S— available from Alford Label, Costa Mesa, Calif.

Preferred friction regions should provide sufficient immediate static friction to allow tearing of the package when the package has been contacted with lubricant. By "immediate" static friction is meant that the material, when tested as described below, provides a sufficient static friction within one second of being contacted with the lubricant. Materials which develop sufficient static friction only after being exposed to the lubricant for a time period greater than one second are less preferred because the initial effort at tearing the package may result in a failure (i.e., the fingers may slip from the bag resulting in a dropped bag and possibly contamination of the sample).

The coefficient of friction of a material that has been contacted with a lubricant is determined as described below. For purposes of this invention the "grip" provided by the friction regions (herein referred to as the "total static friction") is the sum of the static frictions which are developed on each side of the package (i.e., one side of the package being in contact with a thumb of a hand and the other side being in contact with a finger, usually the forefinger, of the same hand). Each hand (i.e., each thumb and finger pressure pair) develops its own total static friction on each side of the cut and thereby imparts a tearing force. The lesser of the value of the total static friction of each hand is considered the total static friction of a friction region.

The friction regions are positioned to provide a sufficient grip for each hand (i.e., a separate grip region for each hand on each side of the cut) thereby allowing for the easy tearing of the package sheet when a lubricant is contacting the package. More preferably, the friction regions, in addition to being on both sides of the cut, are positioned on both sides of the package (i.e., a first friction region on the thumb side of the package and a second friction region on the finger side of the package).

In one presently preferred embodiment of the friction regions are provided as a pair of matte-finish (non-glossy) paper "labels" adhered to the outer surface of the package. The labels are adhered to the package crossing a cut (e.g., using a pressure sensitive adhesive or a hot-melt rubber cement) and on opposite sides of the package. If desired a single suitable label may be wrapped or folded over the edge of the package and thereby adhere to both outer surfaces of the package (i.e., "on opposite sides" as previously mentioned).

As previously mentioned, the friction regions may be provided next to a cut at any convenient seam. Preferably, the cut and friction region are located near the middle of a seam so that the package is roughly torn in two equal halves.

It is anticipated that a minimum of one friction region that allows a suitable grip to be exerted on both sides of the cut be provided. Alternatively, the friction region may be provided on both sides of the package or at more than one cut. Alternatively, the friction regions may be positioned on opposite sides of the package such that a first friction region on the first side of the package provide a suitable grip on one side of the cut and a second friction region on the second side of the package provide a suitable grip on the other side of the cut.

FIGS. 8a and 8b show the position of cuts 140 and 142 on various seams of the package. At least one such cut is required. FIGS. 8a and 8b also show the position of the friction regions 146 that are positioned as described above on both sides of the cut and preferably on both sides of the package. The size of the friction regions depicted in FIGS. 8a and 8b are not intended to be limiting. If desired larger or smaller friction regions may be employed as discussed previously.

FIG. 9 shows an alternative embodiment of the present invention. The cut and friction regions may be on one or both of the end seals or on the fin seal.

Figure 11:
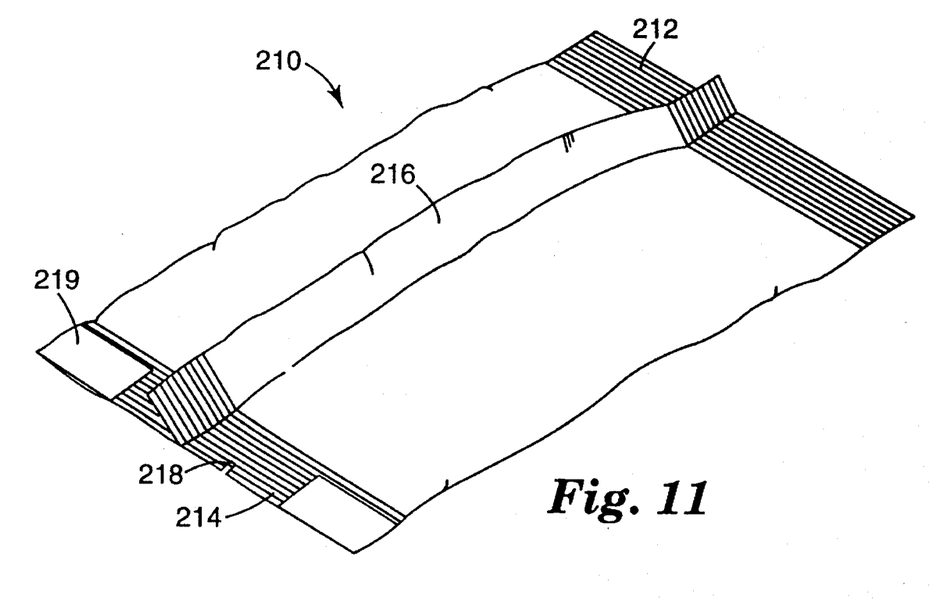
FIG. 11 is a perspective view of another embodiment of the pouch of the invention.

FIG. 11 illustrates another embodiment of the invention, in which a generally elongate friction region 219 formed of adhesive backed paper material 219 is laminated to the laminate material adjacent edge seal 214 of pouch 210. The paper material 219 may have a length, for example, of six inches (15 cm) and the width of the pouch 210 may be approximately four inches (10 cm) so that one inch (2.5 cm) end portions of the paper material 219 are folded over along the upper side of the heat seal 214 in FIG. 11. The elongate paper material 219 is laminated to the laminate material before the heat seals 212, 214 and 216 are formed, and the elongate paper material 219 is folded over during the process of forming the heat seals 212, 214 and 216. The notch 218 is preferably cut into the end seal 214 and paper material 219.

The following examples are offered to aid in the understanding of the present invention and are not to be construed as limiting the scope thereof. Unless otherwise indicated, all parts and percentages are by weight.

EXAMPLES

Test for Determining the Static Coefficient of Friction

Determination of the frictional properties of many materials is often measured in terms of the coefficient of friction. This type of measurement may be made when sliding the material of interest over itself or over another object. The coefficient of friction is a dimensionless term which quantifies the frictional properties and may distinguish between surfaces of varying roughness, tackiness, slipperiness, etc. In the present application, a wide variety of lubricating properties are generated by surfactants or other surface active materials which are added either directly to the casting resins prior to coating the scrim or applied to precoated tape, etc. Although serving the primary purpose of reducing the tack between the casting material and the applier's hands or gloves the lubricants often come in contact with the outer surface of the air and water impermeable package that encloses the casting material. The lubricants have the undesirable effect of rendering the outer surface of the package slippery thereby making the package difficult to grip and tear open. The present invention provides a package of casting material comprising at least one friction region that allows a person to effectively "grip" the package and tear it open. By "grip" is meant the total static friction force produced on a sheet material by a person exerting a reasonable pressure (i.e., a comfortable pressure and not a painful pressure) between their opposing thumb and finger.

A test has been developed which measures the relative grip provided by the friction region, i.e., the static friction between the friction region and a latex glove material. This test method is based on ASTM test method D 1894-87 ("Static and Kinetic Coefficients of Friction of Plastic Film and Sheeting") and measures the static coefficient of friction between a horizontal stationary piece of test specimen and a 200 g 304 stainless steel sled covered with a latex coating. The procedure and apparatus of ASTM test method D 1894 have been modified as described herein. This method yields empirical data which, for the most part, correlates with actual performance of the friction region and thereby offers a quantitative measurement of the grip properties of a given friction region material (when contacted with a standard lubricant solution).

As used herein, the following terms have the following meanings:

"Static Friction"—the resisting or opposing force that arises when a surface of one object starts to slide over the surface of another object.

"Static Coefficient of Friction"—("SCOF") the ratio of the static frictional force to the force acting perpendicularly to the two surfaces in contact (usually the gravitational force). This dimensionless term is a measure of the relative difficulty with which the two materials will initially start to slide across one another i.e., the higher the static coefficient of friction the more difficult it is to start to slide the two materials over one another. The static coefficient of friction, as used herein, is determined from the test described hereinafter and is calculated by the equation:

$$SCOF = \frac{\text{force required to start the sled (g)}}{200 \text{ (g)}}$$

Test Method

SAMPLE AND MATERIALS CONDITIONING

Sample Conditioning—Test samples should be conditioned at 21°–25° C. for not less than 1 hour prior to testing.

Water Conditioning—Water for use in this test should be deionized or soft water conditioned to 22°–24° C.

Test Conditions—Testing must be conducted in a controlled temperature and humidity environment of 21°–25° C. and 45–55% relative humidity.

APPARATUS

Sled—A 304 stainless steel half round cylinder 4.92 cm diameter by 2.54 cm wide and 2.54 cm high with a 4–40 0.5 inch thread in one end into which an Instron part no. T53-5 eye screw is fastened. Material is added or removed from the top of the sled so as to adjust the weight to 200±0.5 g. The radiused face of the sled is coated with a layer of double stick tape (#401 available from Minnesota Mining and Manufacturing Company, St. Paul, Minn.) which is then covered with a latex strip cut from a typical latex glove (Conform™ #69-205, available from Ansell Edmont Industries, Inc., Coshorton, Ohio).

Test Fixture—The Instron Coefficient of Friction Fixture (Catalog No. 2810-005) had previously been modified to accommodate testing of casting materials. Specifically, the pulley assembly was raised 2.54 cm and an additional Teflon™ coated brass tension pulley 0.953 cm in diameter× 13.34 cm was fixed to the end of the table opposite the load pulley and positioned such that the top of the pulley was in the plane of the table.

Force Measuring Device—An Instron Model No. 1122 table top measuring instrument equipped with a 222.4 Newton load cell (Instron assembly No. A-30-39) and connected to an Instron Microcon II microprocessor Model No. MC4100.

PREPARATION OF APPARATUS

1. Assemble the apparatus as described above.
2. Set the drive speed of the sled (i.e. the crosshead speed) to 127 cm/min.
3. Calibrate the 222.4N load cell using a 500 g weight.
4. The following settings on the control panel of the Instron Model No. 1122 measuring device should be set: crosshead speed=127 cm/min; full scale load=0–22.24N; chart speed=12.7 cm/min auto; load cell filter=in; polarity= up.
5. Set up the chart recorder to measure the peak tension force for travel between 0.0 and 2.54 cm.

PROCEDURE

The following procedure is appropriate for testing the static friction of various friction region materials which have been contacted with a lubricant. This procedure is also used to determine static coefficient of friction on "immediately" contacted materials by eliminating the 10 second waiting time after the material has been contacted with the lubricant solution (step #3).

1. Cut the friction region sample to obtain a strip having a width of at least 25.4 mm and a length of at least 50 mm. Place the sample flat on the testing table and fix one end into the hold down clamp.
2. Spray the surface of the sample with approximately 1.2 grams of a lubricant solution comprising 0.28 percent Pluronic™ F-108 in deionized water.

3. 10 seconds after the specimen has been contacted with the lubricant solution, gently place the sled on the specimen such that the wire is straight without sagging and under 10–15 g tension.

4. Within 1 seconds after the sled has been placed on the specimen start the driving mechanism which was previously adjusted to a crosshead speed of 127 cm/min.

5. Record the peak tension force for travel between 0.0 and 2.54 cm.

6. Remove the sled and immediately clean the sliding surface with a soft paper towel. Allow the sled to dry.

EXAMPLE 1

Comparison of Static Friction of a Standard Outer Material and a Matte-finish Paper Friction Region Material Using the aforementioned test method the static coefficient of frictions of a standard packaging material and a matte-finish paper friction region material were measured.

A lubricating solution was prepared by mixing 1.4 gm Pluronic™ F-108 (available from BASF Wyandotte, Parsippany, N.J.) and 500 ml deionized water. This solution was formulated to provide to a non-slippery orthopedic casting material (such as Delta-Lite™ "S", available from the Johnson and Johnson Orthopaedics Inc., Raynham, Mass.) approximately the amount of lubrication that a typical non-tacky orthopedic casting material (such as "Scotchcast™ Plus™", available from Minnesota Mining and Manufacturing Company, St. Paul, Minn.) exhibits when dipped in water and rubbed with a gloved hand. The lubricant solution was sprayed on the test material prior to measuring the frictional properties.

For this measurement the stainless steel sled was covered with a latex rubber surface. Thus the test apparatus measured the frictional properties between the test material and a latex glove material under conditions designed to simulate the actual "wet" conditions encountered when one tries to open a package that has been contacted with a lubricant (e.g., by contact with a wet glove that has been rubbing a slippery casting material from a previously opened roll or has been dipped into an activator solution containing a lubricant).

A sheet of standard packaging material was laid flat on the Instron Coefficient of Friction Fixture and tested as described herein. The sheet was a four ply laminate comprising one layer each of Surlyn™ #1652 ionomer resin, aluminum foil (0.089 mm thick), low density polyethylene, and polypropylene (0.0254 mm thick). The laminate was positioned in the fixture with the polypropylene layer facing up (i.e., the polypropylene layer was positioned to contact the sled). To the laminate was sprayed approximately 1.2 grams of the aforementioned lubricant solution. After waiting ten seconds the latex coated sled was placed on the laminate and pulled across the laminate as described above. The mean static friction force of ten runs was calculated to be 21.1 grams (standard deviation "$\sigma$"=3.45 grams).

A sample of a matte-finish label material (Premium matte coated litho—permanent adhesive" C1S, available from Alford Label, Costa Mesa, Calif.) was tested as described above for use as the friction region material. The label material is coated on one side with a pressure sensitive adhesive suitable for adhering the label to the outer surface of a standard packaging laminate. The label material was positioned and clamped in the test fixture with the matte-finish paper surface facing up (i.e., in position to contact the sled). After contact with the lubricant solution the latex coated sled and matte-finish material produced a mean static friction of 136.2 grams ($\sigma$=3.32 grams, n=11).

For comparison these same materials were tested wet but without exposure to the lubricant (i.e., a spray of plain water was employed). The standard laminate material produced a static friction of 183.8 grams ($\sigma$=16.42 grams, n=5) against the latex coated sled, while the matte-finish paper label material produced a static friction of 163.9 grams ($\sigma$=1.53 grams, n=5) against the latex coated sled.

The above data demonstrates that while both the standard package and the matte-finish label material provide good static friction when contacted with plain water the standard laminate material exhibits a large drop in static friction (hence loss of "grip") when contacted with a lubricant solution. In contrast, the matte-finish label material provides a good "grip" even when contacted with a lubricant solution.

EXAMPLE 2

Comparison of "Immediate" Static Friction of a Standard Outer Material and a Matte-finish Paper Friction Region Material Using the aforementioned test method the immediate static coefficient of frictions of a standard packaging material and a matte-finish paper friction region material were measured.

A lubricating solution was prepared as described in Example 1. A sheet of standard packaging material was laid flat on the Instron Coefficient of Friction Fixture and tested as described herein. The sheet was a four ply laminate comprising one layer each of Surlyn™ #1652 ionomer resin, aluminum foil (0.089 mm thick), low density polyethylene, and polypropylene (0.0254 mm thick). The laminate was positioned in the fixture with the polypropylene layer facing up (i.e., the polypropylene layer was positioned to contact the sled). To the laminate was sprayed approximately 1.2 grams of the aforementioned lubricant solution. Without waiting the latex coated sled was immediately placed on the laminate and pulled across the laminate as described above. The mean immediate static friction force of ten runs (ten separate samples of laminate material were tested) was calculated to be 31.2 grams ($\sigma$=11.9 grams).

A sample of a matte-finish label material (as described in Example 1) was tested as described above for use as the friction region material. The label material was positioned and clamped in the test fixture with the matte-finish paper surface facing up (i.e., in position to contact the sled). After contact with the lubricant solution the latex coated sled and matte-finish material produced a mean immediate static friction of 102.6 grams ($\sigma$=3.2 grams, n=10).

A sample of a gloss-finish label material ("Premium gloss coated litho—permanent adhesive" C1S, available from Alford Label, Costa Mesa, Calif.) was tested as described above for use as the friction region material. The label material was positioned and clamped in the test fixture with the gloss-finish paper surface facing up (i.e., in position to contact the sled). After contact with the lubricant solution the latex coated sled and gloss-finish material produced a mean immediate static friction of 63.5 grams ($\sigma$=6.3 grams, n=10).

The above data demonstrates that the gloss-finish label material provides a lower immediate static friction when contacted with a lubricant solution than a matte-finish material. Furthermore, the matte-finish label material provides a good immediate "grip" even when contacted with a lubricant solution.

Most preferably, the cut is provided in the heat seal at one end of the package between adjacent fibers, and a friction region on both sides of the package adjacent the cut.

Furthermore, although multi-layer laminate sheet materials with four or more layers are discussed above, it will also be understood that the use of fibers within two or three layer laminate sheet materials are contemplated. In that embodiment, the fiber(s) would be laminated between an inner and outer layer of material.

It is to be understood that even though numerous characteristics and advantages of the present invention have been set forth in the foregoing description, together with details of one preferred apparatus used to practice the present invention, the disclosure is illustrative only, and changes may be made in details, especially in matters of details which fall within the principles of the invention to the full extent indicated by the broad, general meaning of the terms in which the appended claims are expressed.

We claim:

1. A kit of orthopedic casting/splinting materials comprising:
   a) a sheet of curable casting/splinting material;
   b) a substantially hermetic pouch containing the curable casting/splinting material, the pouch comprising:
      1) laminate sheet material having opposite side edges, and an outer layer and a heat sealable inner layer bonded to the outer layer;
      2) a heat seal bonding at least a portion of the inner layer of the laminate sheet material to form the pouch, the heat seal bonding the laminate material to form opposite ends of the pouch, the ends of pouch defining a first direction extending between the ends and a second direction extending generally perpendicularly with respect to the first direction; and
      3) means for facilitating tearing of the laminate sheet material in the first direction, the means comprising at least three generally parallel fibers substantially equally spaced apart and disposed between the inner and outer layers, the fibers extending substantially along the first direction to guide tearing the pouch along the first direction, the fibers being substantially equally spaced apart along the laminate sheet material across substantially the entire extent of the laminate sheet material in the second direction such that the distance between either side edge of the laminate sheet material and at least one fiber is no greater than the distance the fibers are spaced apart.

2. A kit according to claim 1, wherein the curable casting material is moisture curable.

3. A kit according to claim 2, wherein the curable casting material contains an isocyanate-functional resin.

4. A kit according to claim 1, wherein the fibers have ends contained within the heat seal.

5. A kit according to claim 1, wherein the laminate sheet material further comprises an interior layer laminated between the inner and outer layers.

6. A kit according to claim 5, wherein the fibers are disposed between the interior and inner layers.

7. A kit according to claim 5, wherein the fibers are disposed between the interior and outer layers.

8. A kit according to claim 5, wherein the interior layer further comprises a metal foil highly impervious to air and water vapor.

9. A kit according to claim 5, wherein the inner layer further comprises a heat sealable plastic resin film laminated to the interior layer.

10. A kit according to claim 1 wherein each fiber comprises a multifilament fiber.

11. A kit according to claim 10 wherein the multifilament fiber is formed of material selected from the group consisting of glass and aromatic polyamide fiber.

12. A kit according to claim 11 wherein each multifilament fiber is formed of glass filaments.

13. A kit according to claim 1 wherein the fibers are substantially equally spaced apart on approximately 25 mm centers across the width of the pouch.

14. A kit according to claim 1 wherein each fiber has a nominal diameter of approximately 0.008 millimeters.

15. A kit of orthopedic casting/splinting materials comprising:
   a) a sheet of moisture-curable casting/splinting material and a lubricant; and
   b) a substantially hermetic heat sealed pouch containing the curable casting/splinting material and lubricant, the pouch comprising:
      1) laminate sheet material having opposite side edges, and further comprising a heat sealable resin film inner layer bonded to a first major surface of a vapor barrier layer and an outer layer bonded to a second major surface of the vapor barrier layer;
      2) a heat seal bonding at least a portion of the inner layer of the laminate sheet material together to form the pouch, the heat seal bonding the laminate material to form opposite ends of the pouch, the ends of the pouch defining a first direction extending between the ends and a second direction extending generally perpendicularly with respect to the first direction; and
      3) means for facilitating tearing of the laminate sheet material, the means comprising:
         at least three generally parallel fibers substantially equally spaced apart and disposed between the inner and outer layers, the fibers extending substantially along the first direction to guide tearing the pouch along the first direction, the fibers being substantially equally spaced apart along the laminate sheet material across substantially the entire extent of the laminate sheet material in the second direction such that the distance between either side edge of the laminate sheet material and at least one fiber is no greater than the distance the fibers are spaced apart;
         at least one friction region positioned on the outer layer generally adjacent one of the opposite ends of the pouch adjacent the heat seal, the friction region comprising an adhesively backed paper material adhered to the outer layer; and
         a notch extending inwardly from the end of the pouch generally adjacent the friction region.

16. A kit according to claim 15 wherein the vapor barrier layer comprises a metal foil highly impervious to air and water vapor.

17. A kit according to claim 15 wherein each fiber comprises a multifilament fiber, the material of the multifilament fiber being selected from the group consisting of glass and aromatic polyamide fiber.

18. A kit according to claim 17 wherein each fiber comprises a multifilament fiber.

19. A kit according to claim 17 wherein each multifilament fiber is formed of glass filaments.

20. A kit according to claim 17 wherein the paper material provides a mean immediate total static friction of at least 100 grams when contacted with the lubricant.

21. A kit according to claim 20 wherein the laminate material further comprises an interior layer between the inner and outer layers, the interior layer comprising a metal foil and the outer layer comprising a puncture resistant outer material laminated to the metal foil.

22. A kit according to claim 21 wherein the friction region provides a mean immediate total static friction of at least 150 grams when contacted with the lubricant.

23. A kit according to claim 15 wherein the friction region provides a mean immediate total static friction of at least 180 grams when contacted with the lubricant.

24. A kit according to claim 15 wherein the friction region comprises a matte-finish paper material having a surface area of at least 100 square millimeters.

25. A kit according to claim 24 wherein the notch extends into the friction region.

26. A kit according to claim 15 wherein the notch extends into the friction region.

27. A kit according to claim 25 wherein the pouch has opposite sides extending between the opposite ends, the friction region comprises two friction regions, one on each side of the pouch adjacent one of the opposite ends of the pouch.

28. A kit according to claim 15 wherein the friction region comprises a water-absorbing element.

29. A substantially hermetic heat sealed pouch comprising:
   a) laminate sheet material having opposite side edges, and a heat sealable inner layer bonded to an outer layer;
   b) a heat seal bonding at least a portion of the inner layer of the laminate sheet material to form the pouch, the heat seal bonding the laminate material to form opposite ends of the pouch, the ends of the pouch defining a first direction extending between the ends and a second direction extending generally perpendicularly with respect to the first direction; and
   c) means for facilitating tearing of the laminate sheet material in the first direction, the means comprising at least three generally parallel fibers substantially equally spaced apart and disposed between the inner and outer layers, the fibers extending substantially along the first direction to guide tearing the pouch in the first direction, the fibers being substantially equally spaced apart along the laminate sheet material across substantially the entire extent of the laminate sheet material in the second direction such that the distance between either side edges of the laminate sheet material and at least one fiber is no greater than the distance the fibers are spaced apart.

30. A pouch according to claim 29, wherein the fibers have ends contained within the heat seal.

31. A pouch according to claim 29, wherein the laminate sheet material further comprises an interior layer laminated between the inner and outer layers.

32. A pouch according to claim 31, wherein the fibers are disposed between the interior and inner layers.

33. A pouch according to claim 31, wherein the fibers are disposed between the interior and outer layers.

34. A pouch according to claim 31, wherein the interior layer further comprises a metal foil highly impervious to air and water vapor.

35. A pouch according to claim 30, wherein the inner layer further comprises a heat sealable plastic resin film laminated to the interior layer.

36. A pouch according to claim 30, wherein each fiber comprises a multifilament fiber, the material of the multifilament fiber being selected from the group consisting of glass and aromatic polyamide fiber.

37. A pouch according to claim 36, wherein each multifilament fiber is formed of glass filaments.

* * * * *